(12) United States Patent
DeShazo

(10) Patent No.: US 11,121,624 B1
(45) Date of Patent: Sep. 14, 2021

(54) CONFIGURABLE MULTI-OUTPUT CHARGE PUMP

(71) Applicant: ADVANCED NEUROMODULATION SYSTEMS, INC., Plano, TX (US)

(72) Inventor: Daran DeShazo, Lewisville, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

(21) Appl. No.: 16/992,954

(22) Filed: Aug. 13, 2020

(51) Int. Cl.
*H02M 3/07* (2006.01)
*H02M 3/157* (2006.01)

(52) U.S. Cl.
CPC ............ *H02M 3/07* (2013.01); *H02M 3/157* (2013.01)

(58) Field of Classification Search
None
See application file for complete search history.

(56) References Cited

U.S. PATENT DOCUMENTS

| | | | |
|---|---|---|---|
| 5,948,004 A | 9/1999 | Weijand et al. | |
| 7,804,256 B2 * | 9/2010 | Melanson | H05B 45/37 315/291 |
| 7,805,189 B2 | 9/2010 | Stein et al. | |
| 7,923,865 B2 | 4/2011 | Melse | |
| 7,982,529 B2 | 7/2011 | Tranchina et al. | |
| 9,352,162 B2 | 5/2016 | Lamont et al. | |
| 9,985,634 B2 * | 5/2018 | Ulrich | H04L 25/0272 |
| 2004/0167407 A1 | 8/2004 | Roberts | |
| 2012/0163632 A1 * | 6/2012 | Lesso | H02M 3/07 381/107 |
| 2016/0285363 A1 * | 9/2016 | Englekirk | H02M 3/07 |
| 2017/0099011 A1 * | 4/2017 | Freeman | H02M 1/44 |
| 2019/0207514 A1 * | 7/2019 | Yu | H02M 3/07 |

* cited by examiner

*Primary Examiner* — Lincoln D Donovan
*Assistant Examiner* — Khareem E Almo

(57) ABSTRACT

A configurable multi-output charge pump for power supply generation includes one or more flying capacitors (FCs) arranged to be switchably connected into a plurality of circuit configurations operative to provide respective output voltages at a common charging node. A configuration logic circuit is operative to generate one or more configuration setting control signals to effectuate a particular circuit configuration. One or more storage capacitors (SC) are independently and individually connectable to the common charging node depending on a selection control logic having a configurable duty cycle, wherein each SC is operative to supply a respective voltage output to drive a corresponding electrical load.

14 Claims, 9 Drawing Sheets

PROVIDING CHARGING CIRCUITRY INCLUDING ONE OR MORE FLYING CAPACITORS (FCS) ARRANGED TO BE SWITCHABLY CONNECTED INTO A PLURALITY OF CIRCUIT CONFIGURATIONS, EACH OPERATIVE TO PROVIDE AT A COMMON CHARGING NODE A VOLTAGE THAT IS A MULTIPLE OF AN INPUT VOLTAGE ⸺ 702

PROVIDING STORAGE CAPACITOR CIRCUITRY INCLUDING ONE OR MORE STORAGE CAPACITORS (SCS) EACH ARRANGED TO BE SWITCHABLY CONNECTED TO THE COMMON CHARGING NODE, WHEREIN AN SC IS OPERATIVE TO BE CHARGED TO A PARTICULAR VOLTAGE DEPENDING ON WHICH CIRCUIT CONFIGURATION OF THE CHARGING CIRCUITRY IS DRIVING THE COMMON CHARGING NODE, EACH SC ADAPTED TO SUPPLY A RESPECTIVE VOLTAGE OUTPUT AT A CORRESPONDING OUTPUT NODE ASSOCIATED THEREWITH ⸺ 704

GENERATING ONE OR MORE OUTPUT SELECTION SIGNALS TO ACTUATE A PARTICULAR COMBINATION OF ONE OR MORE SELECTION SWITCHES TO CONTROL WHICH SC IS CONNECTED TO THE COMMON CHARGING NODE FOR A CONFIGURABLE AMOUNT OF TIME ⸺ 706

GENERATING ONE OR MORE CONFIGURATION SETTING CONTROL SIGNALS TO ACTUATE A PARTICULAR COMBINATION OF ONE OR MORE CONFIGURATION SWITCHES TO CONNECT A SELECT SET OF FCS FOR EACH CIRCUIT CONFIGURATION OF THE CHARGING CIRCUITRY, WHEREIN A CHARGE PHASE CONNECTION STATE AND A STORAGE PHASE CONNECTION STATE ARE EFFECTUATED FOR SAID EACH CIRCUIT CONFIGURATION, THE CONFIGURATION SETTING CONTROL SIGNALS RESPONSIVE TO WHICH SC IS SELECTED TO BE CONNECTED TO THE COMMON CHARGING NODE, THEREBY EFFECTUATING A CORRESPONDING CIRCUIT CONFIGURATION FOR GENERATING A PARTICULAR MULTIPLE OF THE INPUT VOLTAGE AT THE COMMON CHARGING NODE ⸺ 708

CONFIGURABLE MULTI-OUTPUT CHARGE PUMP

TECHNICAL FIELD

The present disclosure generally relates to power supply circuitry. More particularly, and not by way of any limitation, the present disclosure is directed to a configurable multi-output charge pump for power supply generation in a neuromodulation system.

BACKGROUND

A variety of devices, apparatuses, electronic systems, etc. (collectively, "systems") employ power supply circuitry in order to provide voltages and/or currents used in operating the system itself or used in the operation of the system. Such power supply circuitry is often utilized to alter power supplied from a power source, such as line power or a battery, to meet the demands or requirements of the system. For example, power supply circuitry may be utilized to step-up/step-down current, step-up/step-down voltage, provide a direct current (DC) output from an alternating current (AC) input, and/or provide an AC output from a DC input. Circuitry providing the foregoing may be relatively complex, perhaps including a number of active components, and often suffers from inefficiencies, e.g., an appreciable amount of the power supply energy is consumed in altering the power supplied from the power source. However, complex and inefficient power supply circuits are undesirable in a number of situations, such as in certain portable devices or systems using a battery as a power supply.

An implantable neurostimulator or neuromodulator is one example of a portable device which may implement power supply circuitry as described above in altering one or more aspects of a battery power supply output for use in operating the device or in the operation of the device. Because implanting and explanting such a neurostimulator causes appreciable trauma to the patient, it is typically desired that the neurostimulator power supply be small and relatively long lasting and that the circuitry (including power supply circuitry) of the neurostimulator be small and reliable. Even where a rechargeable battery is used as a power supply, it is typically desired to provide operation of the neurostimulator in such a way as to result in a relatively long battery life between recharge cycles so as to minimize restrictions on the patient's mobility. Battery voltage associated with a battery such as may be implemented in a neurostimulator can be 2.5 volts, for example, or on the order of 4.2 volts, for lithium ion, but in any case is typically relatively low due to the size constraints of the device.

In providing neurostimulation, it may be desirable to provide up to 30 milliamp pulses, for example, to an area of the patient's anatomy, such as near the spinal cord. The patient equivalent resistance in the area of the delivery of the therapeutic current can often range from 200Ω to 2 kΩ. Knowing the current and load, the voltage needed to effect the desired therapy can be calculated in the above example as being on the order of 15 volts to provide the desired current to the patient. However, as described above, the battery voltage may be much less than 15 volts.

Accordingly, the above-mentioned neurostimulator may implement power supply circuitry that provides voltage up-conversion to facilitate delivery of therapy to the patient using the available power supply. There are many ways to implement voltage up-conversion. However, in a battery-powered device, in particular, it is generally desirable to provide the voltage up-conversion in the most efficient way possible.

Further, when amplitudes and/or patient equivalent resistance is low, stimulation can often be effectively achieved with supply voltages that are less than the battery voltage. Multiplying by factors less than 1 (i.e., in down-conversion) allows for reduction of the battery current drawn by the stimulation circuitry with respect to a particular set of stimulation parameters.

In the past a number of power supply circuit configurations have been implemented to provide voltage conversion, e.g., in particular, inductive voltage up-converters (voltage up-converters also being referred to herein as voltage multipliers) and capacitive voltage up-converters.

Inductive voltage up-converters or voltage multipliers require the use of a coil for voltage conversion, which in turn necessitates the use of alternating current. However, batteries such as those used in the above mentioned neurostimulators provide direct current. Accordingly, the use of an inductive voltage multiplier with a battery power supply generally involves the use of complicated and inefficient switching regulator circuitry to convert the direct current from the battery to alternating current for voltage up-conversion. Moreover, additional rectifier circuitry is typically implemented to convert the up-converted alternating current back to direct current. Electromagnetic noise is often introduced by inductor-based switching regulator circuitry, which may interfere with data communications, thereby requiring additional shielding and/or circuitry to prevent such electromagnetic noise from interfering with operation of the device. Accordingly, inductive voltage up-converters are generally undesirable for use in small battery powered devices, such as implantable neurostimulators.

Capacitive voltage up-converters or voltage multipliers have generally been used to provide output voltages in integer multiples of the battery voltage (e.g., 2 times the battery voltage, 3 times the battery voltage, etc.). However, such integer multiples of the battery voltage often are not the most efficient voltages. For example, assuming a battery voltage of 4 volts and that a desired current for therapeutic stimulation requires 9 volts, a typical prior art capacitive voltage multiplier must provide 12 volts for the needed 9 volt pulse because its design provides selection between 4 volts (1 times the 4 volt battery voltage), 8 volts (2 times the 4 volt battery voltage), 12 volts (3 times the 4 volt battery voltage), etc.

The power consumed from the battery is based on the multiplicative factor created from the battery. In the foregoing example, if 10 milliamps was delivered to the patient, 30 milliamps was pulled from the battery because of the 3 times multiplicative factor used in the voltage up-conversion. Accordingly, if the voltage provided by the power supply circuitry could be controlled to more closely match that needed for the desired level of stimulation, the multiplicative factor, and thus the power pulled from the battery, could be reduced.

Further compounding the inefficiencies associated with capacitive voltage multipliers of the prior art is their operation in creating and storing a voltage multiple. In operation, a capacitive voltage multiplier will create a particular multiply voltage and store that voltage on a storage capacitor for output by the power supply circuit. When it is desired to change the output voltage of the power supply circuit, the previously stored multiply voltage stored by the storage capacitor must be discharged in order to change the voltage to a new value. The discharge of the previously stored multiply voltage is a waste of energy which, if done often, can amount to an appreciable drain on the power supply. For example, where two sequential stimulation pulses of a neurostimulator require different voltages, prior art capacitive voltage multipliers would require discharging of capacitors charged for providing the first voltage in order to facilitate recharging of the capacitors for providing the second voltage, thereby wasting energy.

SUMMARY

Embodiments of the present patent disclosure are directed to a configurable multi-output charge pump and associated method for power supply generation in an electronic system, e.g., a neuromodulation system, wherein one or more independently controllable voltage outputs may be generated for simultaneously driving a corresponding number of circuit loads. In one example embodiment, the charge pump comprises, inter alia, charging circuitry including one or more flying capacitors (FCs) arranged to be switchably connected into a plurality of circuit configurations, each operative to provide at a common charging node a voltage that is a multiple of an input voltage. Storage capacitor circuitry including one or more storage capacitors (SCs) is provided, wherein each SC is arranged to be switchably connected to the common charging node such that an SC is operative to be charged to a particular voltage level depending on which circuit configuration of the charging circuitry is driving the common charging node. In one arrangement, each SC may be adapted to supply a respective voltage output at a corresponding output node associated therewith. A mapping selection logic circuit is included for generating one or more output selection signals operating to actuate a particular combination of one or more selection switches to control which SC is connected to the common charging node for a configurable amount of time. A configuration logic circuit is included for generating one or more configuration setting control signals to actuate a particular combination of one or more configuration switches to connect a select set of FCs for each circuit configuration of the charging circuitry. In one arrangement, the configuration logic circuit is further operative to effectuate a charge phase connection state and a storage phase connection state for each circuit configuration. In one arrangement, the configuration logic circuit is further operative in response to a determination as to which SC is selected to be connected to the common charging node, thereby effectuating a corresponding circuit configuration for generating a particular multiple of the input voltage at the common charging node.

In one arrangement, an example charge pump may include a mapping selection logic circuit that comprises a mapping decoder operative to decode an x-bit mapping control signal into [n] output selection signals, where $x=\log_2(n)$ and [n] is a maximum number of SCs independently connectable to a common charging node of the charge pump. In one arrangement, the mapping selection logic circuit is operative in response to one or more duty cycle control signals configured to provide duty cycle information with respect to the x-bit mapping control signal for indicating which SC of the charge pump is to be connected to the common charging node for what duration of time. In one arrangement, the duty cycle information with respect to the x-bit mapping control signal may be optimized based on respective current loads expected be drawn from one or more SCs depending on corresponding load circuitry coupled to each SC. In one arrangement, an example charge pump may include a configuration logic circuit that comprises a configuration decoder operative to decode a y-bit configuration control signal into [p] configuration setting control signals, where $y=\log_2(p)$ and [p] is a maximum number of circuit configurations into which one or more FCs of charging circuitry can be connected. In one arrangement, an example charge pump may include a clock generator to generate a charge phase control signal, a storage phase control signal and a latch signal, wherein the charge phase control signal and the storage phase control signal have complementary logic states with respect to each other and are separated for a select time period during which the latch signal is asserted. A charge phase combinational logic circuit may be included that is operative in response to the charge phase control signal and a particular configuration setting control signal that is latched for a select duration of time for actuating a particular set of configuration switches to cause the selected FC circuit configuration in a charge phase. In similar fashion, a store phase combinational logic circuit operative in response to the storage phase control signal and the particular configuration setting control signal may be provided for actuating a particular set of configuration switches to cause the selected FC circuit configuration in a store phase. In one arrangement, an example charge pump may include power selection and switching circuitry for selecting among an input voltage and one or more secondary voltage supplies, which may comprise voltage outputs of the charge pump itself, for powering the configuration switches to connect a select set of FCs depending on a selected circuit configuration of the charging circuitry. In one arrangement, an example charge pump may comprise a number of FCs that may be configured to provide at the common charging node a voltage that is one or more fractional and/or integer multiples of the input voltage, e.g., ¼VIN to 4 times of VIN in a 3-FC arrangement.

In another aspect, an embodiment of an implantable medical device (IMD) operative in a biostimulation system is disclosed, wherein the IMD comprises, inter alia, a power supply module, a processing unit and associated digital control logic, and a configurable multi-output charge pump operative in response the processing unit and associated digital control logic for generating a plurality of voltage outputs that are independently connectable to a common charging node based on a duty cycle for simultaneously driving a corresponding number of electrical loads. In yet another aspect, a power supply generation method involving a configurable multi-output charge pump is disclosed.

Additional/alternative features and variations of the embodiments as well as the advantages thereof will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

FIGS. 7A-7D depict flowcharts illustrative of blocks, steps and/or acts that may be (re)combined in one or more arrangements with or without additional flowcharts of the present disclosure for facilitating a power supply generation method according to some embodiments.

DETAILED DESCRIPTION

Figure 1:
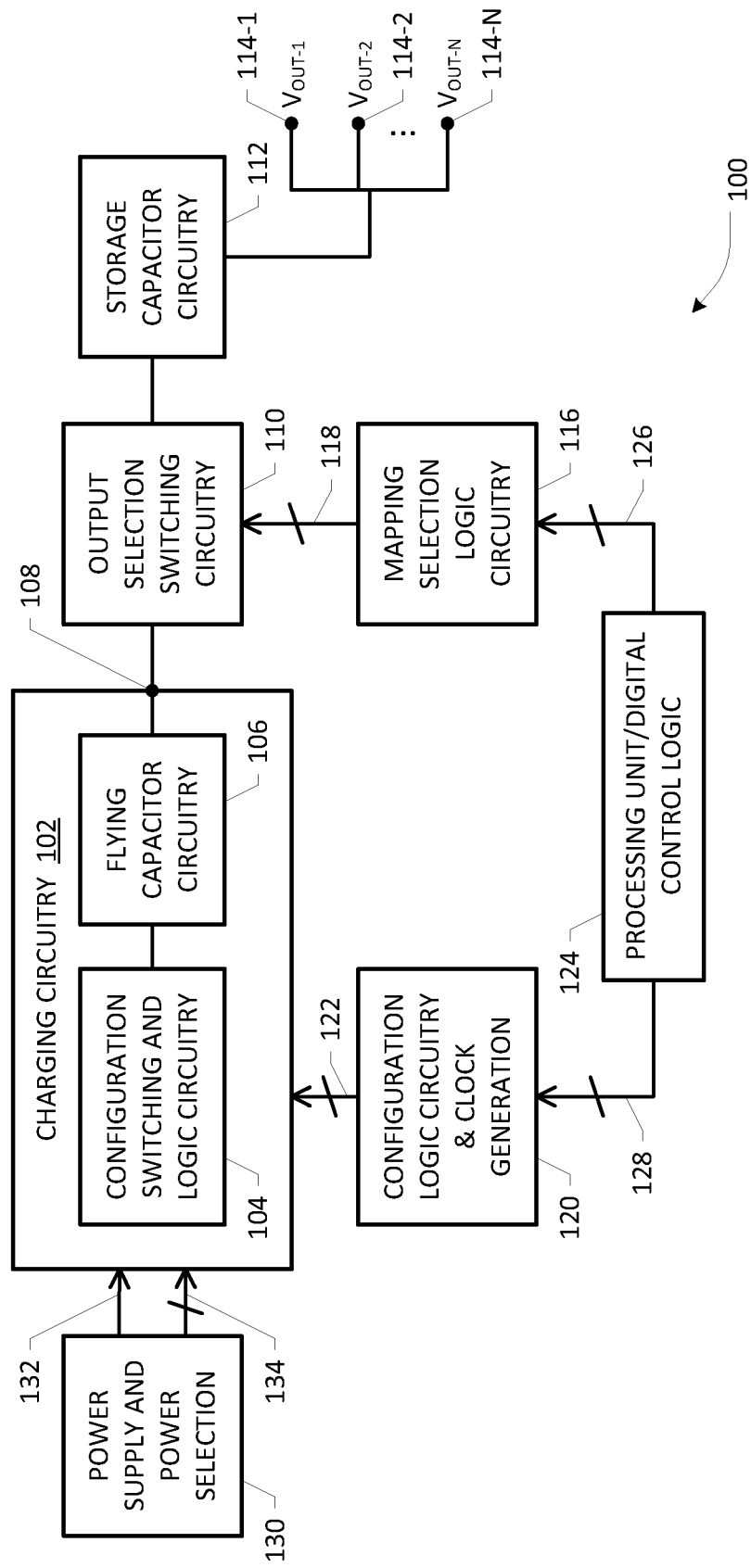
FIG. 1 depicts a circuit block diagram of a configurable multi-output charge pump for power supply generation in an example system according to an embodiment of the present patent disclosure.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some example embodiments described herein may relate to power supply arrangements with respect to an implantable pulse generator (IPG) or neuromodulator for providing therapy to a desired area of a body or tissue based on a suitable stimulation therapy application, such as a spinal cord stimulation (SCS) system or other neuromodulation systems. However, it should be understood that example embodiments disclosed herein are not limited thereto, but have broad applicability, including but not limited to therapy applications involving different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators or pacemakers, gastric stimulators, and the like, as well as implantable drug delivery/infusion systems, implantable devices configured to effectuate real-time measurement/monitoring of one or more physiological functions of a patient's body (i.e., patient physiometry), including various implantable biomedical sensors and sensing systems. Further, whereas some example therapy applications may involve implantable devices, additional and/or alternative embodiments may involve external personal devices, e.g., wearable biomedical devices, that may be configured with suitable power supply circuitry for providing therapy to the patients analogous to the implantable devices. Accordingly, all such devices may be broadly referred to as "personal medical devices," "personal biomedical instrumentation," or terms of similar import, at least for purposes of some example embodiments of the present disclosure.

Referring to FIG. 1, depicted therein is a circuit block diagram of a configurable multi-output charge pump 100 for facilitating power supply generation in an example system (e.g., an IMD or similar biomedical instrumentation system, etc.), wherein a wide range of supply voltages may be generated according to an embodiment of the present patent disclosure to support multiple circuit portions or loads implemented to achieve different design objectives and electrical functions in the example system. By way of illustration, it should be appreciated that while constant current neuromodulation therapy may render the exact stimulation power supply voltage in a particular therapy system inconsequential, a variety of supply voltages may nevertheless be required to support the varied ranges of current amplitudes that may be delivered over a wide range of patient impedances. Accordingly, example embodiments herein describe a configurable charge pump, e.g., multi-output charge pump 100, that can generate a broad range of voltages through suitable programming logic that may be implemented on-chip, onboard, off-board, or a combination thereof. In addition to being able to charge a single output capacitor to a particular voltage level, embodiments of the charge pump 100 may be configured to charge up multiple output capacitors to provide multiple output voltages in parallel. As will be set forth below, an embodiment may therefore be configured to generate not only various stimulation power supply levels but also a number of voltages for auxiliary circuits using a single set of flying capacitors (FCs) and an appropriate number of storage capacitors (SCs) to meet the different electrical demands in an example therapy system.

In one arrangement, charge pump 100 may comprise charging circuitry 102 including one or more FCs (e.g., M capacitors forming FC circuitry 106), which may be switchably connected into a plurality of circuit configurations using suitable switching circuitry and associated control logic 104 that may be selectively actuated in response to one or more configuration setting control signals 122 generated from a configuration logic and clock generation circuit 120. In one example implementation, each FC circuit configuration may be arranged to provide, at a common node 108, which may be referred to as a charging node herein, a voltage that is a multiple of an input voltage supplied by a suitable power supply and power selection circuitry 130. In one implementation, input voltage may be provided by a battery, a regulated voltage generator, etc., which may be selectably connected by one or more power selection switches to an input supply path 132 associated with the charging circuitry 102. Power selection circuitry 130 may also be operative to supply, and select between, additional sources of power in some embodiments, whereby additional power paths 134 may be provided to supply power for operating the configuration switching and control logic circuitry 104. Charge pump 100 further includes one or more SCs (e.g., N capacitors forming SC circuitry 112), wherein each is SC arranged to be switchably connected to the common charging node 108 by way of an output selection switching circuit block 110 that may be selectively actuated in response to one or more output selection control signals 118 generated from a mapping selection logic circuit 116. By selectively actuating a particular output selection switch combination, a select SC is operative to be connected to the common charging node 108 whereby the selected SC may be charged (i.e., "pumped") to a particular voltage level depending on which circuit configuration of the charging circuitry 102 is driving the common charging node 108. Accordingly, each SC may be adapted to supply a respective voltage output at a corresponding output node associated therewith, as illustrated by $V_{OUT-1}$ 114-1 to $V_{OUT-N}$ 114-N in FIG. 1. Further, each output voltage node may be coupled to a corresponding circuit load (not shown in FIG. 1), whereby appropriate levels of power, voltage and/or current may be provided to thereto depending on the overall system design in which the charge pump 100 may be implemented.

According to some embodiments, mapping selection logic circuit 116 is operative to generate output selection control signals 118 that may be appropriately duty-cycled in order to control which SC is connected to the common charging node 108 for a configurable amount of time depending on the current draw expected from each SC. In one implementation, suitable control signals 126 may be provided by digital control logic and/or associated processing unit circuitry 124 that may be either external to, associated with or otherwise integrated with the charge pump circuitry, wherein the control signals 126 are configured to provide duty cycle information with respect to indicating which SC of the charge pump 100 is to be connected to the common charging node 108 for what duration of time. Responsive thereto, a particular configuration of the output selection control signals 118 may be generated, which in turn operate to control a select combination of output selection switches for coupling the select SC to the charging node 108 as noted above. Skilled artisans will recognize that SC sizes and pumping duty cycles may be optimized using appropriate digital control logic in an example embodiment based on the different current loads that may be expected in an application. For example, an SC (SC1) may be configured for stimulation supply voltage (high demand and larger current load) and another SC (SC2) may be configured for support voltages that are low demand. In such a scenario, SC2 can be sized to have a lower capacitance than SC1. Also, SC2 may be re-charged less frequently than SC1 due to the low current draw of the support circuits in a typical implementation. Accordingly, an example embodiment may be advantageously configured to allocate more time for charging an SC that will experience a larger current load by generating a suitably controlled duty cycle that apportions the pumping time among the various SCs by switchably connecting each SC to the charging node 108 for a respectively optimized duration in a time-interleaved fashion.

Figure 2A:
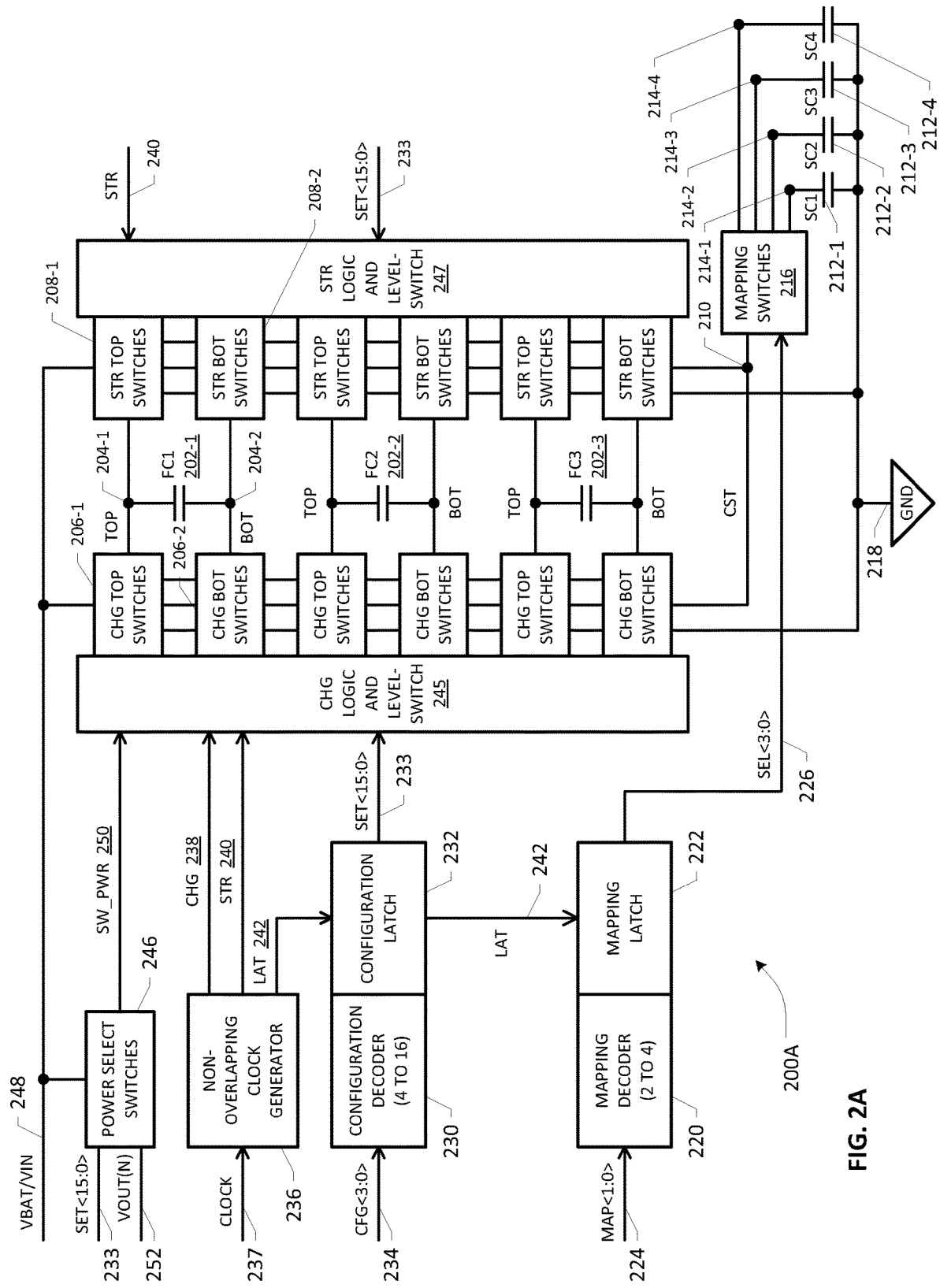
FIG. 2A depicts a circuit block diagram of an example 4-output charge pump having a switchably connectable 3-capacitor arrangement that illustrates additional details according to an embodiment of the present patent disclosure.

In one implementation, configuration setting control signals 122 for actuating a particular combination of one or more configuration switches of circuitry 104 in order to effectuate a select FC circuit configuration may also be generated responsive to appropriate control and timing signals 128 from a suitable digital control logic block. In some arrangements, such digital control logic and/or associated processing unit circuitry may be different from the digital control logic circuitry 124 that provides mapping selection and duty cycle control signals 126. Alternatively, various digital control logic portions configured for controlling the charge pump operations set forth herein may be combined into a single block as exemplified in FIG. 1. Regardless of where the control/timing signals 128 are generated, the configuration logic circuitry 120 is operative to effectuate appropriate connections for a charge phase state and a storage phase for each FC circuit configuration, depending on which SC is selected to be connected to the common charging node 108 in a pumping operation. As one skilled in the art will appreciate upon reference hereto, each SC may be configured to provide a particular output voltage level and a different FC circuit configuration may therefore be effectuated accordingly in order to provide a suitable multiple of the input voltage thereat. Consequently, it will be understood that mapping selection logic and FC configuration logic may operate in a coordinated fashion to control the overall operation of charge pump 100 where the mapping selection functionality may be provided as an outer control loop for selecting which SC is connected in the pumping operation (and for determining the time duration of the connection) and the FC configuration logic functionality may be provided as an inner control loop for determining, and alternating between, the charge phase state connectivity and the storage phase state connectivity for a particular FC configuration corresponding to the selected SC. Set forth below are additional details of the foregoing design architecture of a configurable multi-output charge pump by taking reference to some non-limiting example implementations FIG. 2A depicts a circuit block diagram of an example 4-output charge pump 200A having a switchably connectable 3-capacitor arrangement according to an embodiment of the present patent disclosure. Capacitors 202-1 to 202-3 are operative as FCs that may be switchably configured into different circuit configurations under digital control logic whereas four capacitors 212-1 to 212-4 are provided as SCs in the example charge pump 200A, with each SC having a terminal (e.g., a "TOP" terminal) operative as a respective output voltage node 214-1 to 214-4 that may be connected to different loads as noted previously. Without limitation, one or more capacitors (e.g., FCs 202-1 to 202-3) may be disposed external to the charge pump circuitry in some arrangements. Whereas FCs 202-1 to 202-3 can generally be of low capacitance and small footprint, e.g., in a range of 2.0 µF to 5.0 µF, SCs 212-1 to 212-4 may be larger, e.g., in the range of 10.0 µF to 50.0 µF. Each FC is provided with a "top" terminal (identified as TOP) and a "bottom" terminal (identified as BOT), e.g., as exemplified by TOP 204-1 and BOT 204-2 for FC1 202-1. Further, the TOP and BOT terminals of each FC are each associated with a respective set of switches for connecting the terminal to an input voltage (VIN/VBAT 248), to the terminals of other FCs, or a common node CST 210 under a charge state connection (referred to as a CHARGE or CHG phase) or a store state connection (referred to as a STORE or STR phase). As illustrated, switch circuitry 206-1 and switch circuitry 206-2 exemplify switches operative with TOP terminal 204-1 and BOT terminal 204-2 of FC1 202-1 for the CHARGE phase, respectively. Likewise, switch circuitry 208-1 and switch circuitry 208-2 exemplify switches operative with TOP terminal 204-1 and BOT terminal 204-2 of FC1 202-1 for the STORE phase, respectively.

In accordance with the teachings herein, CST node 210 may be switchably coupled to any of the SCs under mapping selection logic exemplified by a mapping decoder 220, mapping latch 222 and associated switching circuitry 216. In order to facilitate a selection among four SCs, a 2-to-4 mapping decoder may be provided operating in response to a 2-bit MAP signal 224, which may be provided by a digital control logic block, e.g., circuitry 124 shown in FIG. 1. The 2-bit MAP signal 224 may be decoded and latched responsive to a latch signal 242 as a 4-bit SEL signal 226 where one of the bits is asserted (e.g., logic high) while others are deasserted (e.g., logic low). Responsive to suitable timing control, SEL signal 226 having a particular logic is operative to actuate mapping switching circuitry 216 for selectively coupling a particular one of SC1 212-1 to SC4 212-4 to CST node 210.

To facilitate switchable connectivity of FC1-FC3 into multiple circuit configurations (which can comprise various series or parallel combinations of FCs and input voltage, VIN/VBAT), wherein each circuit configuration is operative to cause a particular multiple of VIN to appear at CST 210, appropriate configuration logic and timing circuitry exemplified by a configuration decoder 230, configuration latch 232 and non-overlapping clock generator 236 may be provided. In order to account for all possible circuit combinations involving three FCs, a 4-to-16 binary decoder may be provided to decode a 4-bit configuration (CFG) signal 234, which may be provided by a digital control logic block, e.g., circuitry 124 shown in FIG. 1. In one arrangement, the 4-bit CFG signal 234 may be decoded and latched responsive to latch signal 242 generated by the clock generator 236 operating in response to a clock signal 237. A 16-bit SET control signal 233 operative as a configuration setting control signal may therefore be generated accordingly, wherein one of the bits is asserted (e.g., logic high) while remaining 15 bits are deasserted (e.g., logic low). The clock generator circuit 236 is also operative to generate two additional control signals, CHG 238 and STR 240, operating as phase selection signals for alternating and transitioning between the CHARGE and STORE phases, respectively, for each FC circuit configuration.

Appropriate digital logic 245, 247, operative as switch control logic, may be provided to select how the terminals of FCs, VIN/VBAT and CST node need to be connected for each circuit configuration under the CHARGE and STORE phases, respectively. As illustrated, digital logic block 245 is operative to actuate a select combination of switches from the various switch banks associated with each FC responsive to SET signal 233 and CHG signal 238 (for the CHARGE phase). Likewise, digital logic block 247 is operative to actuate a select combination of switches responsive to SET signal 233 and STR signal 240. Generally, digital logic blocks 245, 247 may be implemented using any type of combinational logic involving various logic gates such as AND gates, OR gates, XOR gates, NAND gates, NOR gates, XNOR gates and NOT gates, for example.

In some embodiments, a power select switching network or circuitry 246 may be provided, which is operative in response to SET signal 233 and a plurality of output voltages that may be sourced from one or more SCs, e.g., SC1 212-1 to 212-4, as exemplified by VOUT(N) 252. Power select switching circuitry 246 may be configured to select whether VIN/VBAT or one of the charge pump voltage outputs is used as the power supply (SW_PWR) 250, for powering the FC switch circuitry, e.g., circuitry 206-1, 206-2, 208-1, 208-2. In example operation, a highest value of the output voltages is used (i.e., Max{VOUT(N)}), which may be provided as the output level of the logic and associated level-shifting blocks 245, 247, depending on whether a power supply is directly applied to drive the switches and associated control logic or if suitable voltage partitions are needed accordingly in some embodiments.

Figure 2B:
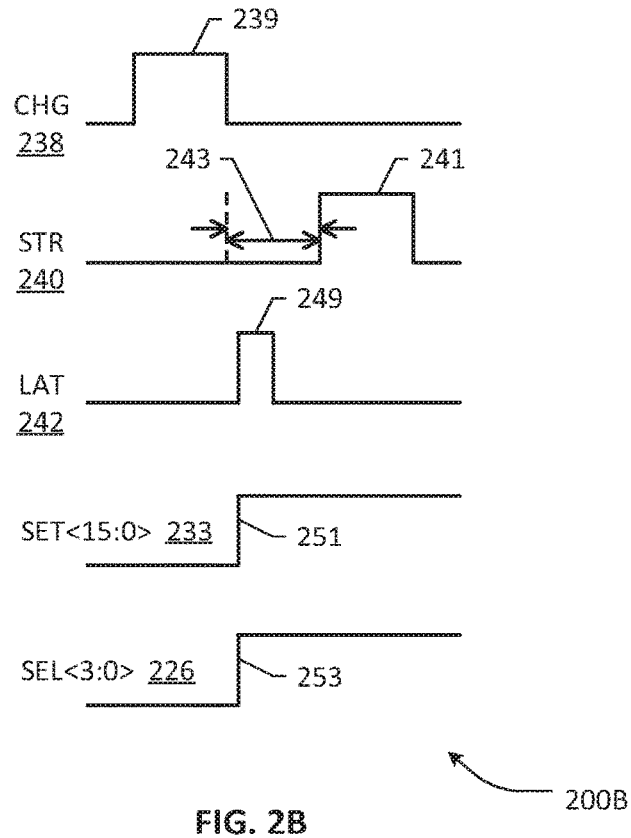
FIG. 2B depicts a panel of timing diagrams associated with various control signals operative in a configurable multi-output charge pump according to an embodiment of the present patent disclosure.

It will be appreciated that CHG signal 238 and STR signal 240 are provided with complementary logic levels and may be configured to be out of phase by having a "dead" time therebetween. In one arrangement, the latched timing of SET signal 233 and SEL signal 226 may be employed in operating the charge pump 200A to force all changes to the SET or SEL signals 233, 226 to occur in the dead time between CHG and STR control signals 238, 240, thereby effectuating the CHARGE and STORE phases for a particular FC circuit configuration in an alternating manner separated by a quiescent period therebetween. This timing control may preferably be provided in an example embodiment so as to ensure that charge is never inadvertently moved from one capacitor to another. Accordingly, an appropriate time duration between the CHG and STR pulses may be configured depending on the particular implementation. Directing attention to FIG. 2B, depicted therein is a panel 200B of timing diagrams associated with various control signals operative in an example configurable multi-output charge pump such as charge pump 200A described above, where CHARGE and STORE phases are exemplified by respective pulses 239 and 241 of CHG signal 238 and STR signal 240 that are separated by a configurable dead time 243. When a change in the capacitor circuit configuration is required (e.g., a different FC circuit configuration is desired based on selecting a different SC), corresponding SET signal 233 and SEL signal 226 are generated, with each having a respective particular bit asserted during the dead time 243. As noted previously, SET signal 233 and SEL signal 226 are latched by LAT signal 242, which is preferably asserted during the dead time 243 as exemplified by a LAT pulse 249. By controlling that transitions between CHARGE and STORE phases as well as changes to a capacitor circuit configuration of the charge pump take place only during the dead time, example embodiments ensure that all FCs and SCs are floating (e.g., relative to a ground or other suitable reference node 218) for a sufficient period of time such that there are no transients in the capacitive elements and/or no charge is inadvertently moved across the capacitors during the transitions or configuration changes. It will therefore be realized that because SCs are generally larger in an example charge pump implementation, and may even have different sizes, an appropriate amount of dead time may need to be configured to account for the transients in the largest SC in order to properly time the switching circuitry for facilitating the SC's switchable connection to the charge pump's CST node.

Figure 3:
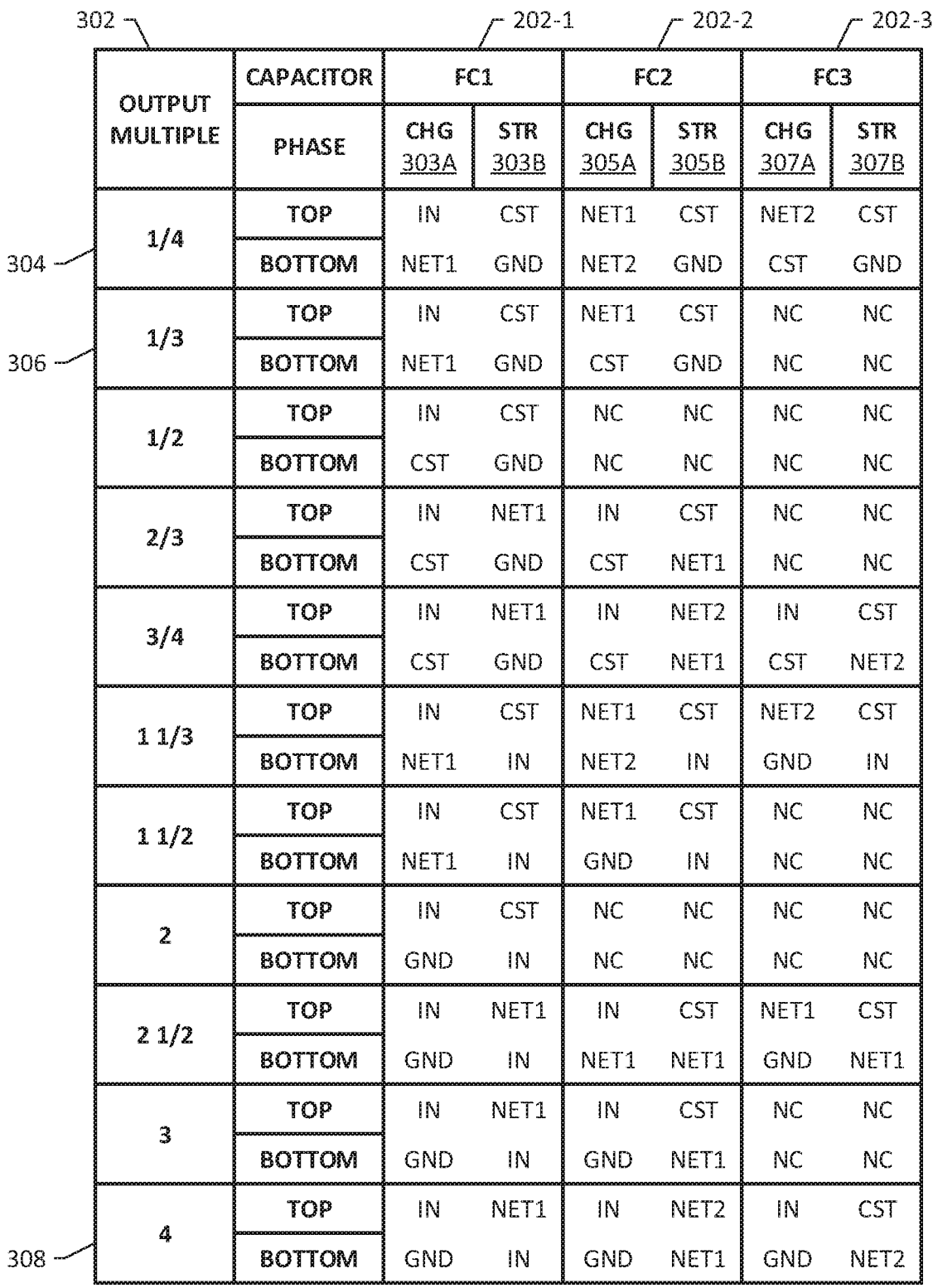
FIG. 3 depicts a table of connection logic for effectuating various circuit configurations associated with the 3-capacitor arrangement of the charge pump shown in FIG. 2A wherein each circuit configuration is operative to provide a voltage that is a multiple of an input voltage according to an embodiment of the present patent disclosure.

FIG. 3 depicts a connection logic table or a circuit "netlist" 300 for effectuating a plurality of circuit configurations associated with the 3-FC arrangement of the charge pump 200A shown in FIG. 2A, wherein each circuit configuration is operative to generate a voltage that is a multiple of an input voltage (VIN or VBAT) according to an embodiment of the present patent disclosure. An output multiple column 302 illustrates the various fractional or integer multiples of the input voltage that may be generated at CST node 210 in either CHARGE or STORE phase. Columns 303A, 305A, 307A illustrate connections for TOP and BOT terminals of each FC 202-1 to 202-3, respectively, in the CHARGE phase, for each output voltage level. Likewise, columns 303B, 305B, 307B illustrate connections for TOP and BOT terminals of each FC 202-1 to 202-3, respectively, in the STORE phase, for each output voltage level. By way of example, to obtain an output voltage level of ¼VIN as illustrated in row 304, the following connectivity is effectuated in the CHARGE phase: TOP terminal of FC1 is connected to VIN (as shown by IN), BOT terminal of FC1 is connected to TOP terminal of FC2 (as indicated by a common connection node NET1), BOT terminal of FC2 is connected to TOP terminal of FC3 (as indicated by a common connection NET2) and BOT terminal of FC3 is connected to CST. In similar fashion, the following connectivity is effectuated in the STORE phase for the output voltage level of ¼VIN: TOP terminals of all FCs are connected to CST while BOT terminals of all FCs are connected to ground (as indicated by GND). In either of the CHARGE or STORE phases, one of the SC terminals may be switchably connected to CST, which SC terminal is operative as a supply node to an external circuit load as described previously.

It will be seen that not all FCs need to be connected in a circuit configuration for obtaining a particular output voltage. For example, the following connectivity is effectuated in the CHARGE phase for the output voltage level of ⅓VIN as indicated in row 306: TOP terminal of FC1 is connected to VIN (as shown by IN), BOT terminal of FC1 is connected to TOP terminal of FC2 (as indicated by a common connection NET1) and BOT terminal of FC2 is connected to CST. The STORE phase connectivity for the output voltage level of ⅓VIN is as follows: TOP terminals of both FC1 and F2 are connected to CST while BOT terminals of FC1 and FC2 are connected to GND. In either of these phases, FC3 remains unconnected, as indicated by NC (Not Connected) identifier in row 306 of the connection logic table 300.

As illustrated in FIG. 3, example charge pump 200A is operative to provide output voltages levels from ¼VIN to 4 times VIN using different FC circuit configurations effectuated by the connection logic table 300. Regardless of how many SCs are provided to drive a corresponding number of circuit loads, the example charge pump is operative to charge each SC to a respective voltage level (which may be dependent on what the expected current draw is from each load). Accordingly, any given number of SCs may be configured to operate as independent power supplies, wherein the SCs may be switchably coupled to the charging node 210 based on a load-dependent duty cycle and different FC circuit configurations may be switched dynamically based on the appropriate combinational logic as previously noted.

Figure 4:
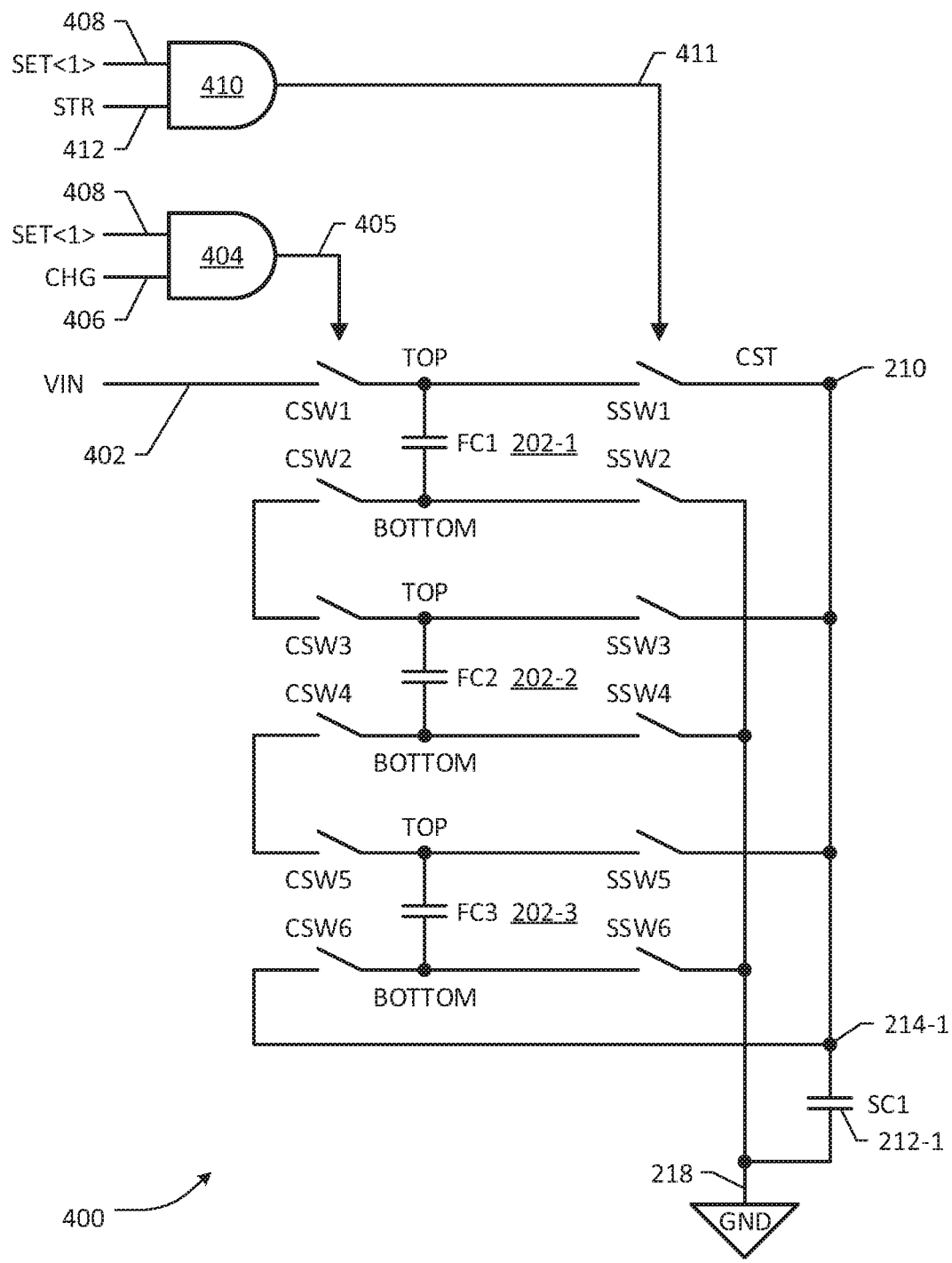
FIG. 4 depicts an example circuit configuration and associated switching circuitry for generating a ¼ fractional multiple of an input voltage using the charge pump of FIG. 2A.

FIG. 4 depicts a circuit diagram 400 illustrating example circuit configuration and associated switching circuitry for generating a ¼ fractional multiple of an input voltage using an example 3-FC charge pump (e.g., charge pump 200A of FIG. 2A). Switches CSW1-CSW6 and switches SSW1-SSW6 are exemplary of switching circuitry used for effectuating connectivity among FC1 202-1 to FC3 202-3 in CHARGE and STORE phases, respectively, relative to VIN node 402 and CST 210. In particular, switches CSW1-SSW1 and switches CSW2-SSW2 are associated with TOP and BOT terminals of FC1 202-1, switches CSW3-SSW3 and switches CSW4-SSW4 are associated with TOP and BOT terminals of FC2 202-2, and switches CSW5-SSW5 and switches CSW6-SSW6 are associated with TOP and BOT terminals of FC3 202-3. Switches CSW1-CSW6 are commonly driven by logic signal 405 generated by a logic AND gate 404 that receives a CHG signal 406 and a SET<1> signal 408 as inputs, where <1> is shown as an arbitrary bit of a 16-bit decoded and latched configuration setting signal. Likewise, switches SSW1-SSW6 are driven by logic signal 411 generated by a logic AND gate 410 that receives an STR signal 412 and the SET<1> signal 408 as inputs. As noted above, CHG signal 406 and STR signal 412 have complementary logic levels for alternating between the CHARGE and STORE phases. When both CHG 406 and SET<1> 408 are asserted, signal 405 is generated in the CHARGE phase, causing CSW1-CSW6 to be turned on, i.e., enabled or otherwise actuated, while SSW1-SSW6 are turned off since signal 411 is deasserted or logic low. Accordingly, a series connection of the FCs is effectuated wherein TOP terminal of FC1 is connected to VIN, BOT terminal of FC1 is connected to TOP terminal of FC2, BOT terminal of FC2 is connected to TOP terminal of FC3, and BOT terminal of FC3 is connected to CST 210, which is coupled to a TOP terminal of an example SC, e.g., SC1 212-1, that is operative as output node 214-1 relative to an external load (not shown in this FIG.).

Figure 5:
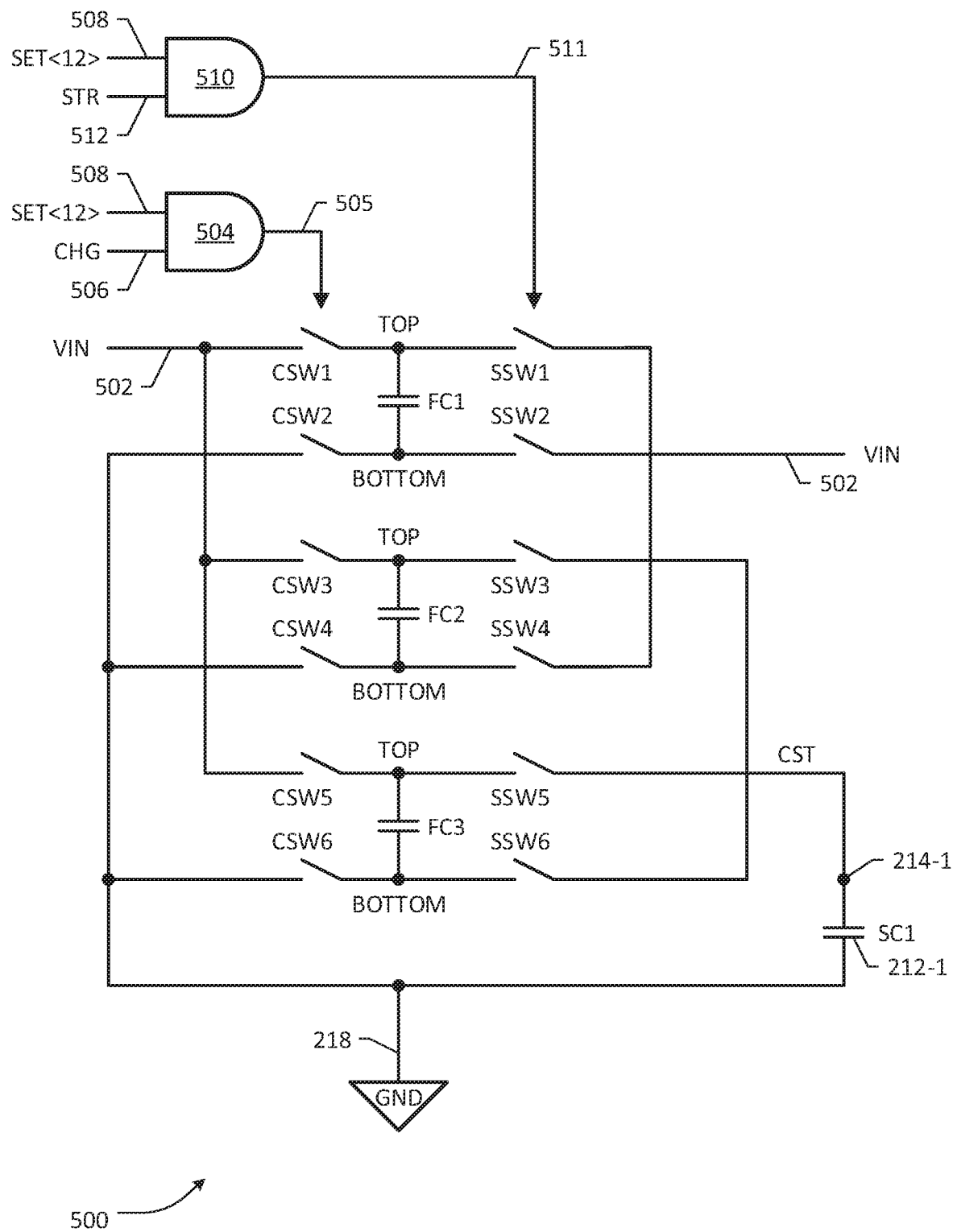
FIG. 5 depicts an example circuit configuration and associated switching circuitry for generating an output voltage that is 4 times an input voltage using the charge pump of FIG. 2A.

In similar fashion, when both STR 412 and SET<1> 408 are asserted, signal 411 is generated in the STORE phase, causing SSW1-SSW6 to be turned on, i.e., enabled or otherwise actuated, while CSW1-CSW6 are turned off since signal 405 is deasserted or logic low. Accordingly, a parallel connection of the FCs is effectuated wherein TOP terminals of FC1-FC3 are connected to CST while BOT terminals of FC1-FC3 are connected to ground or GND 218. As can be appreciated, the foregoing connection schemes are in accord with the connection logic of netlist table 300 shown in FIG. 3 for effectuating an output voltage level comprising the ¼ fractional multiple of VIN FIG. 5 depicts a circuit diagram 500 illustrating example circuit configuration and associated switching circuitry for generating for an output voltage that is 4 times an input voltage using an example 3-FC charge pump (e.g., charge pump 200A of FIG. 2A). Similar to the circuit arrangement 400 of FIG. 4, switch control logic circuitry comprising logic AND gates 504, 510 are provided for generating control signals 505, 511 with respect to CHARGE and STORE phases, respectively. Gates 504, 510 are operative responsive to CHG 506 and STR 512 in combination with a SET<12> signal 508, respectively, where <12> is shown as an arbitrary bit of a 16-bit decoded and latched configuration setting signal. When both CHG 506 and SET<12> 408 are asserted, signal 505 is generated in the CHARGE phase, causing CSW1-CSW6 to be turned on, i.e., enabled or otherwise actuated, while SSW1-SSW6 are turned off since signal 511 is deasserted or logic low. Accordingly, a connection scheme of the FCs is effectuated in the CHARGE phase wherein all TOP terminals of FC1-FC3 are connected to VIN 502 while all BOT terminals of FC1-FC3 are connected to GND 218. In similar manner, when both STR 508 and SET<12> 408 are asserted, signal 511 is generated in the STORE phase, causing SSW1-SSW6 to be turned on, i.e., enabled or otherwise actuated, while CSW1-CSW6 are turned off since signal 505 is deasserted or logic low. Accordingly, the following connection scheme of the FCs is effectuated in the STORE phase: BOT terminal of FC1 is connected to VIN 502 while TOP terminal of FC1 is connected to BOT terminal of FC2, TOP terminal of FC2 is connected to BOT terminal of FC3, and TOP terminal of FC3 is connected to CST. Skilled artisans will recognize that the foregoing connection schemes are in accord with the connection logic 308 of netlist table 300 shown in FIG. 3 for effectuating an output voltage level comprising 4 times VIN.

Although a single AND gate is illustrated in the switch control logic circuitry of the foregoing embodiments with respect to each of the CHARGE and STORE phases, it should be understood that such logic circuitry may involve more logic gates and/or different types of logic gates depending on how many states of an FC arrangement need to be turned on in order to obtain a particular circuit configuration. In some embodiments, therefore, the general form of the combinational logic for all CHG switches may be such that each switch may be driven by an AND gate that is driven by CHG signal and the OR of all SET states which require that switch turned on, e.g., CHG AND (SET<1> OR SET<5>). Likewise, the general form of the combinational logic for all STR switches may be such that each switch may driven by an AND gate that is driven by STR signal and the OR of all SET states which require that switch turned on, e.g., STR AND (SET<2> OR SET<4>). Accordingly, each FC terminal may be connected to an array of switches activatable by appropriate control signals depending on the decoded SET signals that may vary from configuration to configuration.

Controllable switching circuitry utilized in coupling various FCs in different circuit configurations as well as to select power sources and/or output SCs according to the teachings of the present disclosure may be implemented using a variety of electronic devices. Such switching circuitry may preferably be configured to provide a "break-before-make" connection so as to avoid overlapping connection of components between various circuit configurations (e.g., between a CHARGE phase circuit configuration and a STORE phase circuit configuration) in additional and/or alternative embodiments. The foregoing switching circuitry may be comprised of solid state circuitry such as, e.g., including but not limited to diodes, bipolar junction transistors (BJTs), metal oxide semiconductor field effect transistors (MOSFETS), junction gate FETs (JFETs), n-channel MOSFET (NMOS) devices, p-channel MOSFET (PMOS) devices, depletion-mode or enhancement-mode devices, micro-electromechanical systems (MEMS) devices (e.g., thermally actuated MEMS, electrostatically actuated MEMS, electromagnetically actuated MEMS), etc., as well as any digital switching devices built therefrom.

Figure 6:
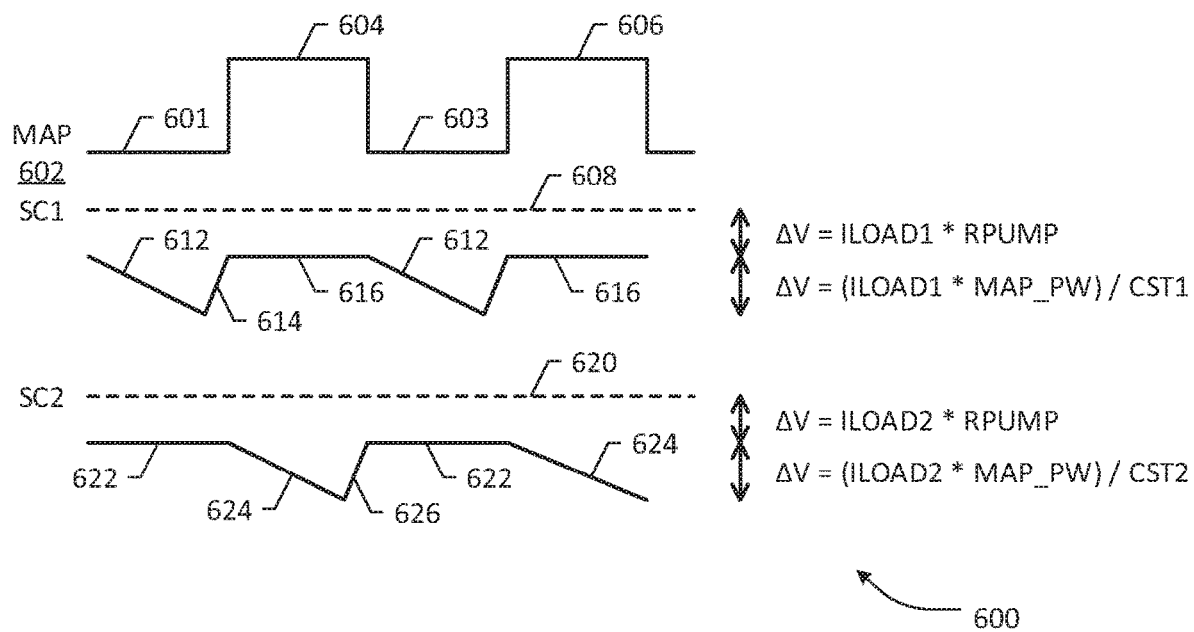
FIG. 6 depicts a panel of timing diagrams associated with a 2-output charge pump configured for simultaneously supplying two electrical loads based on two switchable storage capacitors according to an example embodiment of the present patent disclosure.

FIG. 6 depicts a panel 600 of timing diagrams associated with a 2-output charge pump simultaneously supplying two electrical loads based on two corresponding storage capacitors, SC1 and SC2, according to an example embodiment of the present patent disclosure. A MAP signal 602 is illustrative of a duty cycle indicating switchable connectivity of SC1 and SC2 with a charging node, wherein each SC is charged to an unloaded voltage level 608 and 620, respectively. When the electrical loads (for instance, drawing DC in this illustrative example) are connected to the respective SC1 and SC2 and the MAP signal switches between them, the output voltage of an SC will switch between (i) a constant voltage that is less than the unloaded voltage by a series resistance drop when the MAP signal connects that SC and (ii) a falling voltage due to the capacitive drop when the MAP signal disconnects that SC and connects the other SC. Because SC1 and SC2 may have different electrical characteristics, respective falling voltage traces (e.g., when disconnected) and rising voltage traces (e.g., when (re)connected) of the two SCs may be different. By way of example, when MAP signal 602 is logic low as indicated by levels 601, 603, SC1 is disconnected while SC2 is connected. Likewise, when MAP signal 602 is logic high as indicated by levels 604, 606, SC1 is connected while SC2 is disconnected. Accordingly, the series resistance drop for SC1 when it is connected to CST is shown as $\Delta V = ILOAD1 * RPUMP$, resulting in a constant voltage level 616 during when MAP signal 602 is high, where ILOAD1 is the current draw of a first electrical load (LOAD1) and RPUMP is the charge pump resistance. In similar fashion, the series resistance drop for SC2 when it is connected to CST is shown as $\Delta V = ILOAD2 * RPUMP$, where ILOAD2 is the current draw of a second electrical load (LOAD2) and RPUMP is the charge pump resistance, resulting in a constant voltage level 622 during when MAP signal 602 is low.

Capacitive voltage drop for SC1 when it is disconnected from CST (i.e., when MAP signal 602 is low) is shown as $\Delta V = [ILOAD1 * MAP\_PW]/CST1$, where ILOAD1 is the current draw of LOAD1, MAP_PW is the time duration when MAP signal 602 is low, and CST1 is the capacitance value of SC1. In FIG. 6, voltage traces 612 exemplify falling voltage traces involving the capacitive voltage drop when MAP signal 602 is pointing away from SC1. When MAP signal 602 becomes high again, SC1 is (re)connected to CST and the voltage level thereof rises back to the constant voltage level 616, thereby yielding a rising voltage trace 614. Similarly, capacitive voltage drop for SC2 when it is disconnected from CST (i.e., when MAP signal 602 is high) is shown as $\Delta V = [ILOAD2 * MAP\_PW]/CST2$, where ILOAD2 is the current draw of LOAD2, MAP_PW is the time duration when MAP signal 602 is high, and CST2 is the capacitance of SC2. Voltage traces 624 in panel 600 of FIG. 6 exemplify falling voltage traces involving the capacitive voltage drop when MAP signal 602 is pointing away from SC2. When MAP signal 602 becomes low again, SC2 is (re)connected to CST and the voltage level thereof rises back to the constant voltage level 622, thereby yielding a rising voltage trace 626.

FIGS. 7A-7D depict flowcharts illustrative of blocks, steps and/or acts that may be (re)combined in one or more arrangements with or without additional flowcharts of the present disclosure for facilitating a power supply generation method involving a configurable charge pump according to some embodiments. Process flow 700A of FIG. 7A involves providing charging circuitry that includes one or more flying capacitors (FCs) arranged to be switchably connected into a plurality of circuit configurations, wherein each circuit configuration is operative to provide at a common charging node a voltage that is a multiple of an input voltage, as set forth at block 702. Storage capacitor circuitry including one or more storage capacitors (SCs) is provided at block 704, wherein each SC is arranged to be switchably connected to the common charging node. Further, each SC is operative to be charged to a particular voltage depending on which circuit configuration of the charging circuitry is driving the common charging node, wherein each SC adapted to supply a respective voltage output at a corresponding output node associated therewith. At block 706, one or more output selection signals may be generated or otherwise provided to actuate a particular combination of one or more selection switches to control which SC is connected to the common charging node for a configurable amount of time. At block 708, one or more configuration setting control signals may be generated or otherwise provided to actuate a particular combination of one or more configuration switches to connect a select set of FCs for each circuit configuration of the charging circuitry, wherein each circuit configuration may be alternatively transitioned between a charge phase connection state and a storage phase connection state. Also, the configuration setting control signals may be generated responsive to which SC is selected to be connected to the common charging node, thereby effectuating a corresponding circuit configuration for generating a particular multiple of the input voltage at the common charging node.

Figure 7B:
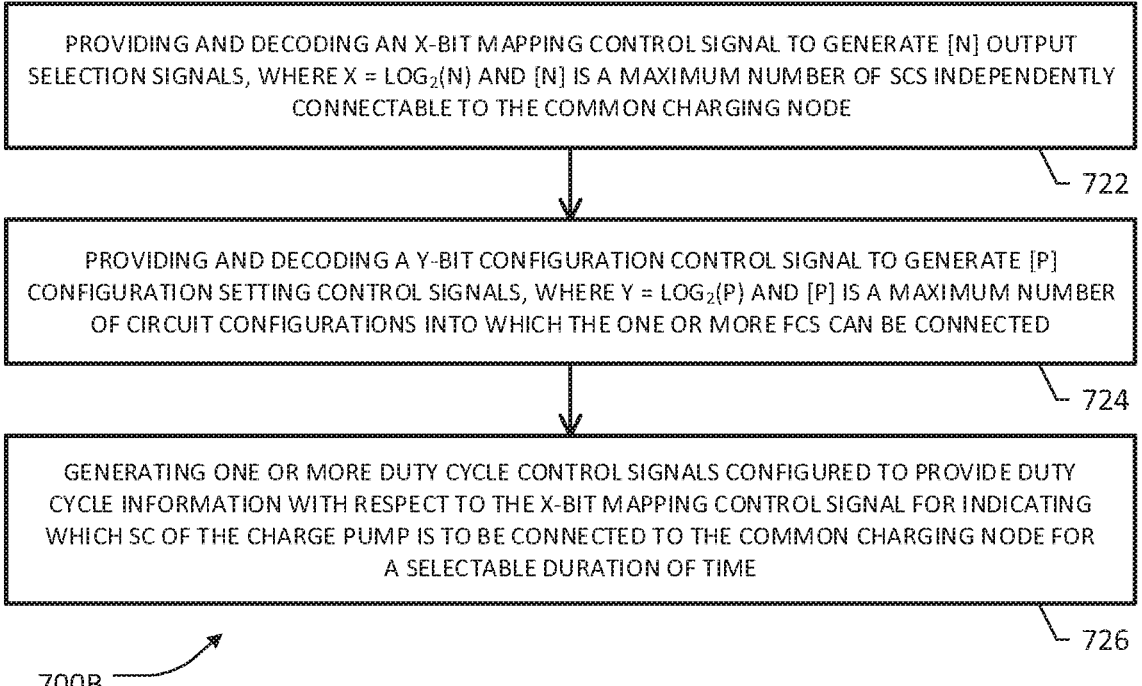

In one example implementation, a power supply generation method may involve providing and decoding an x-bit mapping control signal by a mapping decoder to generate [n] output selection signals, where $x=\log_2(n)$ and [n] is a maximum number of SCs that can be independently connected to the common charging node, as set forth at block 722 of process flow 700B depicted in FIG. 7B. It will be realized that there may be a redundancy in the output selection signals in some arrangements where fewer than the maximum number of SCs that could be supported by the decoded x-bit mapping control signal are provided in an implementation. For example, a 3-bit mapping control signal is needed for selectably switching five SCs although up to eight SCs can be supported by a 3-to-8 binary decoder. At block 724, a y-bit configuration control signal may be provided and decoded by a configuration decoder to generate [p] configuration setting control signals, where $y=\log_2(p)$ and [p] is a maximum number of circuit configurations into which the one or more FCs can be connected. Depending on the number of FCs provided in a charge pump, there may be a redundancy in the configuration setting control signals when [p] is greater than the number of possible circuit configurations. At block 726, one or more duty cycle control signals may be generated that are configured to provide duty cycle information with respect to the x-bit mapping control signal for indicating which SC of the charge pump is to be connected to the common charging node for what duration of time.

Figure 7C:
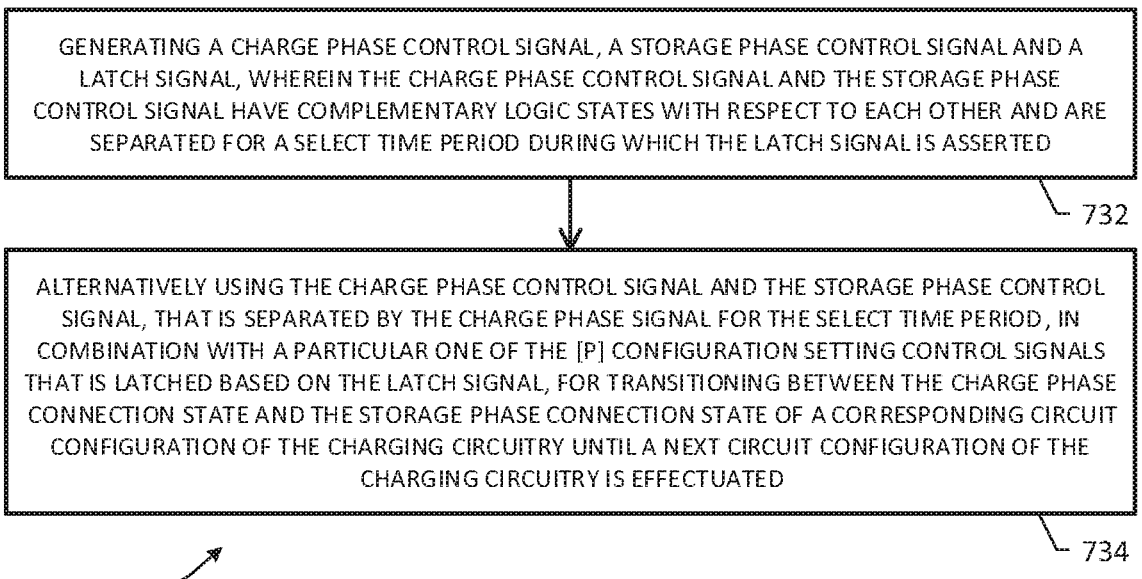
Figure 7D:
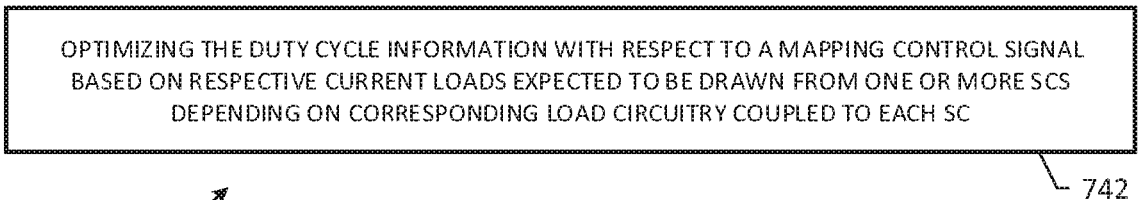

Process flow 700C of FIG. 7C involves generating or otherwise providing a charge phase control signal, a storage phase control signal and a latch signal, wherein the charge phase control signal and the storage phase control signal have complementary logic states with respect to each other and are separated for a select time period during which the latch signal is asserted, as set forth at block 732. Block 734 involves alternatively using the charge phase control signal and the storage phase control signal, that is separated by the charge phase signal for the select time period, in combination with a particular configuration setting control signal that is latched based on the latch signal, for transitioning between the charge phase connection state and the storage phase connection state of a corresponding circuit configuration of the charging circuitry until a next circuit configuration of the charging circuitry is effectuated. Process flow 700D of FIG. 7D involves optimizing the duty cycle information with respect to a mapping control signal based on respective current loads expected be drawn from one or more SCs depending on corresponding load circuitry coupled to each SC, as set forth at block 742.

Figure 8:
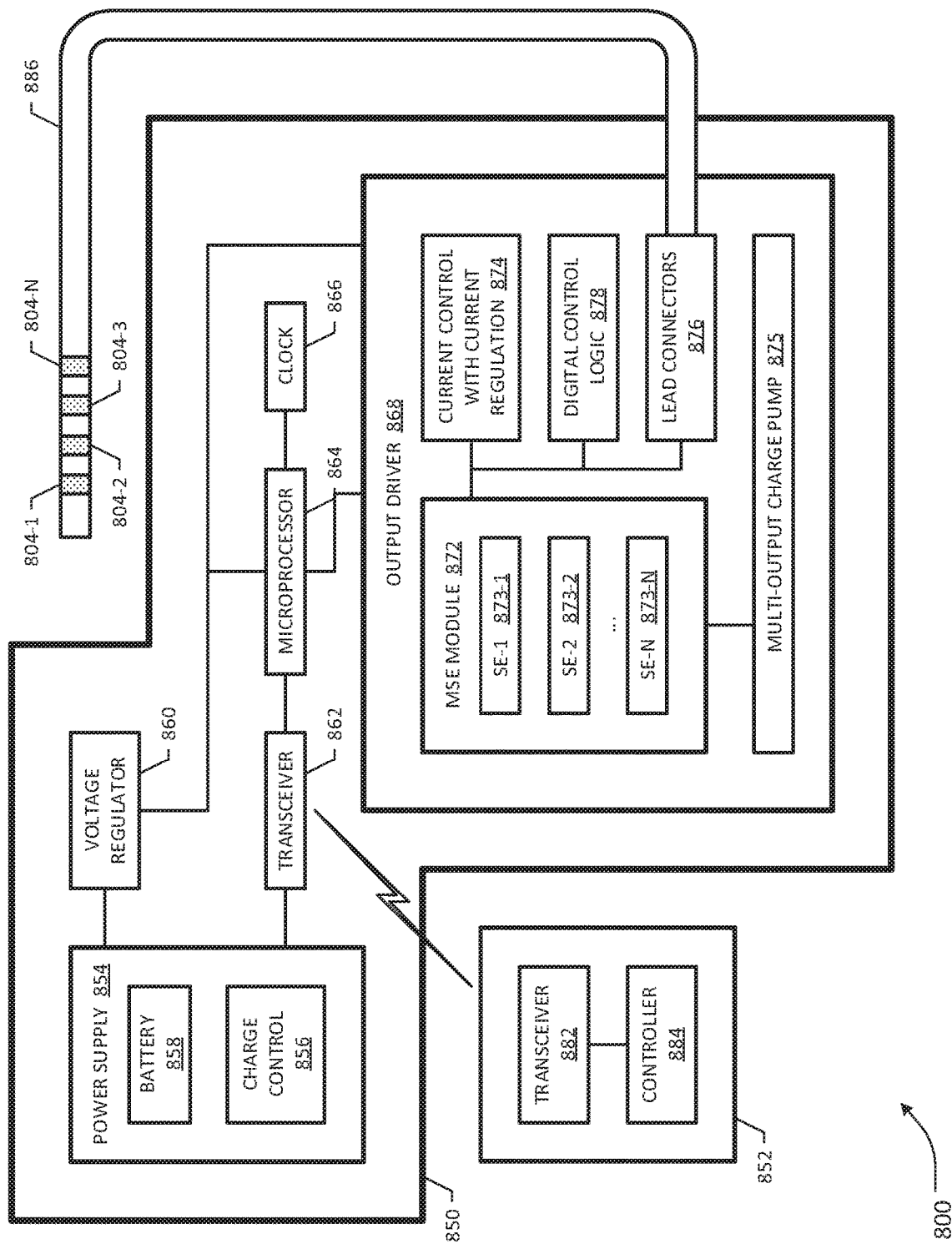
FIG. 8 depicts an example biostimulation system including an implantable medical device wherein a configurable multi-output charge pump may be practiced according to an embodiment of the present patent disclosure.

FIG. 8 depicts an example biostimulation system including an implantable medical device wherein a configurable multi-output charge pump may be practiced according to an embodiment of the present patent disclosure. Stimulation system 800 is adapted to include a generator portion, shown as implantable medical device (IMD) or implantable pulse generator (IPG) 850, providing a stimulation or energy source, a stimulation portion, shown as lead system 886 for application of stimulus pulse(s) to a patient according to a therapy program. An optional external controller, shown as programmer/controller 852, may be provided to program and/or control IPG 850 via a wired/wireless communications link. IPG 850 may be implanted within the body of a human or animal patient (not shown) for providing electrical stimulation from IPG 850 to a selected area of the body via lead 886 under control of external programmer/controller 852.

IPG 850 may be configured as a self-contained implantable pulse generator having an implanted power source such as a long-lasting or rechargeable battery. Alternatively, IPG 850 may comprise an externally-powered implantable pulse generator receiving at least some of the required operating power from an external power transmitter, preferably in the form of a wireless signal, which may be radio frequency (RF)-based (e.g., Bluetooth Low Energy or BLE), via inductive coupling, etc. IPG 850 may includes a voltage regulator 860, power supply 854, transceiver 862, microcontroller (or microprocessor) 864, clock 866, and output driver circuitry 868 comprising a multi-stimulation engine (MSE) 872 having one or more stimulation engines (SEs) 873-1 to 873-N, each having respective power supply requirements. Additionally, a current control/regulation block 874 along with a multi-output charge pump 875 may be provided in some embodiments for operation with stimulation module 872.

Power supply 854 provides a source of power, such as from battery 858 (which may comprise a non-rechargeable battery, e.g., single use battery, a rechargeable battery, a capacitor, and/or like power sources), to other components of IPG 850, as may be regulated by voltage regulator 860 including and/or facilitating digitally-programmable analog voltage generation. Charge control 856 of an example embodiment of IPG 850 is operative to provide recharging management with respect to battery 858. Transceiver 862 of an example embodiment of IPG 850 is operative to provide data/control communication between microprocessor 864 and a controller 884 of external programmer/controller 852 via transceiver 882 provided therewith.

Microprocessor/controller 864 provides overall control with respect to the operation of IPG 850, such as in accordance with a program stored therein or provided thereto by external programmer/controller 852. One or more SEs 873-1 to 873-N of stimulation engine module 872 may be configured to generate and deliver stimulation therapies having suitable pulse characteristics to selected sets or portions of electrodes 804-1 to 804-N under control of microcontroller 864. In one example embodiment, different SEs 873-1 to 873-N of module 872 may be controlled to output optimized stimulation therapies simultaneously without collisions to different sets of electrodes selected under programmatic control. By way of illustration, a stimulation therapy may comprise delivering a constant current pulse of a desired magnitude/amplitude, duration, phase, and frequency to a tissue load via particular ones/sets of electrodes 804-1 to 804-N, which may be represented as respective lumped-element electrode/tissue interface (ETI) loads. Clock 866 preferably provides system timing information, such as may be used by microcontroller 864 in controlling system operation, as well as for different portions of module 872, digital control logic 878 and multi-output charge pump 875 for generating desired voltages, etc., described above in detail.

Lead system 886 of the illustrated embodiment includes a lead body encapsulating a plurality of internal conductors coupled to lead connectors (not shown) to interface with lead connectors 876 of IPG 850 in a hermetically sealed arrangement. The internal conductors provide electrical connection from individual lead connectors to each of a corresponding one of electrodes 804-1 to 804-N, which may be configured to provide anodic current stimulation and/or cathodic current stimulation for application at, or proximate to, a spinal nerve or peripheral nerve, brain tissue, muscle, or other tissue depending on a desired therapy. Skilled artisans will recognize that example therapies may comprise, without limitation, at least one of a spinal cord stimulation (SCS) therapy, a neuromuscular stimulation therapy, a dorsal root ganglion (DRG) stimulation therapy, a deep brain stimulation (DBS) therapy, a cochlear stimulation therapy, a cardiac pacemaker therapy, a cardioverter-defibrillator therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, and a vagal nerve stimulation (VNS) therapy.

In one arrangement, individual SEs 873-1 to 873-N may be configured to provide independently optimized stimulation current while delivering respective therapies simultaneously, each being powered by the multi-output charge pump 875. Stated differently, example SEs 873-1 to 873-N may be independently controlled to output respective electrical signals by varying signal parameters such as intensity, duration and/or frequency in order to deliver a desired therapy and/or otherwise provide optimal stimulation current pulsing using a range of optimized voltages supplied by the multi-output charge pump 875 as described herein.

Although lead 886 is exemplified as a single implantable lead, an example system may involve a lead system comprising two or more implantable leads, with each lead having a respective plurality of electrodes, wherein different combinations of electrodes/leads may be grouped into one or more channels in a stimulation therapy system. Moreover, various types, configurations and shapes of electrodes (and lead connectors) may be used according to some embodiments. Skilled artisans will also recognize that any number of electrodes, and corresponding conductors, may be utilized according to some embodiments. Advantageously, stimulation current pulses according to different therapies may be applied by respective stimulation engines to different portions of electrodes according to a particular channel selection scheme regardless of whether one or more leads and/or one or more sets of electrodes are selected for stimulation.

In some arrangements, programmer/controller 852 may be configured to provide data communication with IPG 850, such as to provide programmatic control, e.g., adjust stimulation settings, selection of SEs, selection and/or electrical polarity configuration of different groups of electrodes to which stimulation pulses are delivered, selection of different levels of output voltages from the charge pump 875, etc.

In addition to supplying varying output voltage levels to support different stimulation protocols independently and simultaneously, an example charge pump of the present disclosure may be configured to as a programmable pre-scaler for a stacking charge pump and a support voltage generator. An example stacking charge pump is described in U.S. Pat. No. 8,446,212, entitled "PULSE GENERATOR HAVING AN EFFICIENT FRACTIONAL VOLTAGE CONVERTER AND METHOD OF USE", which is incorporated by reference herein. In still further arrangements, an embodiment of the multi-output charge pump of the present disclosure may also be used as the only supply voltage generator in an ultra-miniature IPG design operative in a biostimulation system such as one set forth above.

Based on the foregoing, skilled artisans will appreciate that several key benefits and advantages may be realized in the practice of an example embodiment of the present invention. Because the charge pump can be duty-cycled between multiple storage capacitors, different levels of output voltages can be created that are simultaneously available, which obviates the need for having to switch a fairly large storage capacitor of conventional designs to meet different current demands that causes inefficiency. Relatedly, since the current efficiency of a capacitive voltage pump depends on how close to the ideal voltage the charge pump output is, by optimizing the sizes of individual storage capacitors in addition to optimizing their duty cycling based on expected current loads, a better matched range of output voltages may be generated, thereby leading to overall efficiency and battery savings in a system. As multiple stimulation supply capacitors can be provided in a "stacking" operation, rapid voltage optimization can be achieved without requiring many external components or multiple charge pump units in series. As such, a wide range of supply voltages can be delivered in an example multi-output charge pump implementation with a minimal number of components, allowing aggressive IPG/IMD miniaturization, which facilitates better implant and explant procedures that cause less trauma to patients. Furthermore, when implemented as a programmable pre-scaler to optimize the voltage multiplier steps in a therapy being delivered, battery current efficiency is increased because of the increased controllability of the stepping operations.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or non-volatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A charge pump, comprising:
   charging circuitry including one or more flying capacitors (FCs) arranged to be switchably connected into a plurality of circuit configurations, each operative to provide at a common charging node a voltage that is a multiple of an input voltage;
   storage capacitor circuitry including one or more storage capacitors (SCs), each arranged to be switchably connected to the common charging node, wherein an SC is operative to be charged to a particular voltage depending on which circuit configuration of the charging circuitry is driving the common charging node, each SC adapted to supply a respective voltage output at a corresponding output node associated therewith;
   a mapping selection logic circuit for generating one or more output selection signals operating to actuate a particular combination of one or more selection switches to control which SC is connected to the common charging node for a configurable amount of time; and
   a configuration logic circuit for generating one or more configuration setting control signals to actuate a particular combination of one or more configuration switches to connect a select set of FCs for each circuit configuration of the charging circuitry, wherein the configuration logic circuit is operative to effectuate a charge phase connection state and a storage phase connection state for said each circuit configuration, the configuration logic circuit further operating responsive to which SC is selected to be connected to the common charging node, thereby effectuating a corresponding circuit configuration for generating a particular multiple of the input voltage at the common charging node.

2. The charge pump as recited in claim 1, wherein the mapping selection logic circuit includes a mapping decoder operative to decode an x-bit mapping control signal into [n] output selection signals, where $x=\log_2(n)$ and [n] is a maximum number of SCs independently connectable to the common charging node.

3. The charge pump as recited in claim 2, wherein the mapping selection logic circuit is operative in response to one or more duty cycle control signals configured to provide duty cycle information with respect to the x-bit mapping control signal for indicating which SC of the charge pump is to be connected to the common charging node for what duration of time.

4. The charge pump as recited in claim 3, wherein the configuration logic circuit includes a configuration decoder operative to decode a y-bit configuration control signal into [p] configuration setting control signals, where $y=\log_2(p)$ and [p] is a maximum number of circuit configurations into which the one or more FCs can be connected.

5. The charge pump as recited in claim 4, further comprising:
- a clock generator to generate a charge phase control signal, a storage phase control signal and a latch signal, wherein the charge phase control signal and the storage phase control signal have complementary logic states with respect to each other and are separated for a select time period during which the latch signal is asserted;
- charge phase combinational logic circuit operative in response to the charge phase control signal and a particular one of the [p] configuration setting control signals that is latched for a select duration of time based on the latch signal;
- a store phase combinational logic circuit operative in response to the storage phase control signal and the particular one of the [p] configuration setting control signals; and
- power select switching circuitry for selecting between the input voltage and one or more voltage outputs for powering the one or more configuration switches to connect the select set of FCs depending on a selected circuit configuration of the charging circuitry.

6. The charge pump as recited in claim 5, wherein the duty cycle information with respect to the x-bit mapping control signal is optimized based on respective current loads expected be drawn from the one or more SCs depending on corresponding load circuitry coupled to each SC.

7. The charge pump as recited in claim 5, wherein the plurality of circuit configurations are configured to provide at the common charging node a voltage that is one or more fractional multiples of the input voltage.

8. The charge pump as recited in claim 5, wherein the plurality of circuit configurations are configured to provide at the common charging node a voltage that is one or more integer multiples of the input voltage.

9. A power supply generation method, comprising:
- providing charging circuitry including one or more flying capacitors (FCs) arranged to be switchably connected into a plurality of circuit configurations, each operative to provide at a common charging node a voltage that is a multiple of an input voltage;
- providing storage capacitor circuitry including one or more storage capacitors (SCs), each arranged to be switchably connected to the common charging node, wherein an SC is operative to be charged to a particular voltage depending on which circuit configuration of the charging circuitry is driving the common charging node, each SC adapted to supply a respective voltage output at a corresponding output node associated therewith;
- generating one or more output selection signals to actuate a particular combination of one or more selection switches to control which SC is connected to the common charging node for a configurable amount of time; and
- generating one or more configuration setting control signals to actuate a particular combination of one or more configuration switches to connect a select set of FCs for each circuit configuration of the charging circuitry, wherein a charge phase connection state and a storage phase connection state are effectuated for said each circuit configuration, and further wherein the one or more configuration setting control signals are generated responsive to which SC is selected to be connected to the common charging node, thereby effectuating a corresponding circuit configuration for generating a particular multiple of the input voltage at the common charging node.

10. The power supply generation method as recited in claim 9, further comprising decoding an x-bit mapping control signal to generate [n] output selection signals, where $x=\log_2(n)$ and [n] is a maximum number of SCs independently connectable to the common charging node.

11. The power supply generation method as recited in claim 10, further comprising generating one or more duty cycle control signals configured to provide duty cycle information with respect to the x-bit mapping control signal for indicating which SC of the charge pump is to be connected to the common charging node for what duration of time.

12. The power supply generation method as recited in claim 11, further comprising decoding a y-bit configuration control signal to generate [p] configuration setting control signals, where $y=\log_2(p)$ and [p] is a maximum number of circuit configurations into which the one or more FCs can be connected.

13. The power supply generation method as recited in claim 12, further comprising:
- generating a charge phase control signal, a storage phase control signal and a latch signal, wherein the charge phase control signal and the storage phase control signal have complementary logic states with respect to each other and are separated for a select time period during which the latch signal is asserted; and
- alternatively using the charge phase control signal and the storage phase control signal that is separated by the charge phase signal for the select time period, in combination with a particular one of the [p] configuration setting control signals that is latched based on the latch signal, for transitioning between the charge phase connection state and the storage phase connection state of a corresponding circuit configuration of the charging circuitry until a next circuit configuration of the charging circuitry is effectuated.

14. The power supply generation method as recited in claim 13, further comprising optimizing the duty cycle information with respect to the x-bit mapping control signal based on respective current loads expected be drawn from the one or more SCs depending on corresponding load circuitry coupled to each SC.

* * * * *